United States Patent [19]
Frey

[11] Patent Number: 5,607,469
[45] Date of Patent: Mar. 4, 1997

[54] BI-LEAFLET PROSTHETIC HEART VALVE

[75] Inventor: Rainer H. Frey, Starnberg, Germany

[73] Assignee: Inocor GmbH, Starnberg, Germany

[21] Appl. No.: 329,165

[22] Filed: Oct. 26, 1994

[30] Foreign Application Priority Data

Oct. 28, 1993 [DE] Germany ............... 43 36 899.9

[51] Int. Cl.[6] ................................. A61F 2/24
[52] U.S. Cl. ............. 623/2; 137/512.1; 137/527.8
[58] Field of Search ................ 623/2, 900; 137/518, 137/527, 499, 512.1, 527.8

[56] References Cited

U.S. PATENT DOCUMENTS

| | | | |
|---|---|---|---|
| 1,306,391 | 6/1919 | Romanoff | 623/2 |
| 2,877,792 | 3/1959 | Tybus | 137/527 |
| 3,625,249 | 12/1971 | Karr | 137/527 |
| 4,222,408 | 9/1980 | Slaughter, Jr. | 137/499 |
| 4,484,365 | 11/1984 | Murguet et al. | 3/1.5 |
| 4,774,981 | 10/1988 | Mizusawa | 137/527 |
| 4,775,378 | 10/1988 | Knoch et al. | 623/2 |
| 4,908,028 | 3/1990 | Colon et al. | 623/2 |
| 5,116,366 | 5/1992 | Hwang | 623/2 |
| 5,178,631 | 1/1993 | Waits | 623/2 |

FOREIGN PATENT DOCUMENTS

| | | |
|---|---|---|
| 3128704A1 | 2/1983 | Germany . |
| WO89/02254 | 3/1989 | WIPO . |
| 89/02254 | 3/1989 | WIPO ................ 623/2 |

OTHER PUBLICATIONS

Bjork and Lindblom, "The Monostrut Bjork–Shiley Heart Valve", Journal of the American College of Cardiology, vol. 6, No. 5, 1142–1148 (Nov. 1985).

Primary Examiner—Michael J. Milano
Attorney, Agent, or Firm—Pollock, Vande Sande & Priddy

[57] ABSTRACT

A bi-leaflet prosthetic heart valve including a substantially circular valve ring having an inner circumference defining a flow channel for blood flow. An axle secured to the valve ring. The axle is parallel to but not co-linear with a diameter of the valve ring. Two substantially half-moon shaped leaflets are hingedly connected to the axle and pivot independently of each other. The leaflets have different cross-sectional areas. The leaflets move between the closed position wherein the leaflets are both substantially in a plane of the valve ring and substantially include a flow of blood through the flow channel and an open position wherein each of the leaflets are pivoted about the axle with respect to the closed position, thereby permitting blood to flow through the flow channel.

26 Claims, 9 Drawing Sheets

BI-LEAFLET PROSTHETIC HEART VALVE

FIELD OF THE INVENTION

The present invention relates to a bi-leaflet mechanical prosthetic heart valve comprising leaflets that pivot between an open position and a closed position merely as a result of the pressure of the flowing blood. This artificial heart valve may be used in particular for permanent implantation into the human body; and it may be used especially it the aorta position and in the mitral position.

In more detail, the present invention relates to a bi-leaflet prosthetic heart valve comprising an essentially circular valve ring defining a circle and a valve ring plane, and having an inner circumference that defines a flow channel for the blood flow. Further, an axle is secured to the valve ring. Further, this prosthetic heart valve comprises two essentially half-moon-shaped valve leaflets, both of which pivot independently of each other on a common axis. Depending on the direction of blood flow, these leaflets may assume an open position, wherein both leaflets extend essentially at right angles to the valve ring plane, or a closed position, wherein both leaflets extend essentially parallel to the plane of the valve ring, and virtually occlude the flow channel with their combined areas.

BACKGROUND OF THE INVENTION

This kind of bi-leaflet prosthetic heart valve is essentially known from German Offenlegungsschrift 31 28 704 or from International Patent Application WO 89/02254. Known bi-leaflet prostheses comprise a symmetrical structure and design in so far as the outline of both leaflets defines the same area or magnitude of surface area. The leaflets are arranged symmetrically with respect to a standard center plane on the valve ring plane. A longitudinal central axis of the single axle on which the two leaflets pivot is in alignment with one diameter of the valve ring.

The development of mechanical prosthetic heart valves started with the so called ball-cage-prostheses ("Starr-Edwards heart valve"). Development proceeded from the tilting disc prostheses ("Bjork-Shiley heart valve", "Medtronic-Hall heart valve", and "Omnicarbon heart valve") to the bi-leaflet prostheses ("St. Jude Medical heart valve", "Edward-Duromedics heart valve", "Carbomedics heart valve" and "Sorin-Bicarbon heart valve") mainly in use today.

With known bi-leaflet prosthesis heart valves, each leaflet comprises its own device for attachment and/or guidance. In the open position, both leaflets are arranged essentially parallel to and at a distance from each other. This type of arrangement provides essentially three flow zones. One flow zone exists between the leaflets and one flow zone exists between the valve ring and the face of the leaflet facing the blood flow. This arrangement allows a reduction of the pressure gradient and an improved response of the leaflet to any change in blood pressure and direction of blood flow. Also, the arrangement is accompanied by a corresponding reduction in regurgitation and closer resemblance of the blood dynamics to the physiology of the natural valve system.

However, there is still a problem of the risk of thromboembolism. This risk requires a continuously controlled administration of anti-coagulants. Further, the risk may include a persistent hemolysis that may frequently increase years after the valve replacement. In this connection, please refer also to D. Horstkotte, C. Aul and L. Seipel, "Einfluβ von Klappentyp und Klappenfunktion auf die chronische intravasale Haemolyse nach alloprothetischem Mitral—und Aortenklappenersatz" (Influence of valve type and valve function upon chronic intravasal hemolysis after alloprosthetic mitral and aortal valve replacement) in Z. Kardiol., 72, (1983), 119.

Hemolysis results from a damage of blood components being subject to a deformation (erythrocytes) and may be evidenced by the rise in LDH and/or by a drop in haptoglobin in the plasma. Among significant causes of hemolysis are high flow velocities (jet flow), areas of turbulence and turbulent flows, which cause high shearing stresses. The latter occur, in particular, in the boundary layers between adjacent flow zones comprising different velocity profiles. In addition, an asynchronous opening and closing behavior of the two leaflets of an artificial valve causes turbulence and turbulent flows. Moreover, as the leaflet comes closer to the valve ring during the action of closing, mechanical damage to the erythrocytes may be caused. In particular, in the aorta position, flow zones adjacent to the periphery and comprising a high flow velocity may impair the endothelium at the arch in the aorta. In addition, in the case of a symmetrical bi-leaflet aorta prosthesis, one must expect considerable regurgitation due to the duration of time required to close, and further due to the asynchronous closing movement of the two leaflets. In the mitral position, it is not possible to achieve a physiological flow profile in the ventricle with a bi-leaflet prosthesis of symmetrical form, because the two marginal flows impede each other. There is an in adequate scouring of the ventricle. The surgeon is unable to remedy this defect by rotating the symmetrical artificial valve in the plane of the valve ring, because he has to expect an interference with components of aorta valve apparatus.

Testing methods have been developed that allow dissolved and briefly excited molecules of photochromic dye stuffs to demonstrate the flow conditions in a pulsating liquid downstream of an artificial valve. See, for example, Yurechko, V. N. et al. in ASAIO Transactions, 1989, 35, 218–221, or in the International Journal of Artificial Organs, No. 6, 1993, 29–33. As an example, these investigations confirm on the distal side (downstream) of an open "Jude Medical heart valve" a flow profile comprising three distinctive flow zones, each having a different velocity profile.

Using the aforementioned test method of Yurechko, V. N., it was possible to show within the present invention, that relatively simple flow conditions may be obtained downstream of a bi-leaflet prosthesis, both leaflets thereof pivot on a common axis. In the open position the two leaflets are arranged in a V-shaped arrangement. Downstream of this arrangement there is a zone of stagnation, accompanied on each side by a flow zone. The extension of the stagnation zone may be influenced by the angle of opening of the leaflets and by the configuration of the leaflet side facing the flow. A relatively small stagnation zone may be achieved by matching these parameters. Consequently, this type of prosthesis allows a simpler flow profile than other types of bi-leaflet prostheses. A flow profile with only two flow zones creates less turbulence and, consequently, reduces the shearing stress upon the erythrocytes. The necessarily present opening angle of the two V-shaped arranged leaflets accelerates the closing action. A more rapid closing action reduces the loss of energy.

In addition, this form of construction provides for an attachment of the two leaflets to a common axle in a simple, stable and reliable manner. The axle or shaft may comprise an adequate diameter and may be secured reliably to the valve ring. The axle passes through a bore defined by a sleeve that is formed integrally in (a one piece manner) with the leaflet. This results in high stability and reliability. An unintentional removal or detachment of the leaflet is not possible. This is in contrast to previously reported accidents, for example, with the "St. Jude Medical heart valves" (see, for example, Journal of Thorac. Cardiovasc. Surgery, No. 31 (1983) and No. 86 (1983); or, in the case of "Edward-Duromedics heart valves", see, for example, Journal of Thorac. Cardiovasc. Surgery, No. 97 (1984), pages 90–94).

Due to the anatomical features, only a very few options are available when inserting an artificial valve. In most cases, the suture ring is attached to the natural valve ring or to remnants of the valves removed. The position of the coronary ostia and of the aortal seal provides further limitations with respect to the insertion of an aortal prosthesis. In the mitral position, the jet flow during the closing step of the aortal valve following the closing action of a mitral prosthesis has to be considered.

Due to the eccentric suspension of the tilting disc of a tilting disc prothesis, the tilting disc prosthesis provides an asymmetrical distal flow profile. The surgeon may use this fact when orientating the valve in order to come closer to the physiological conditions. See for example Viking O. Bjork and Dan Lindblom, "The Monostrut Bjork-Shiley Heart Valve", in Journal of the American College of Cardiology, Vol. 6, No. 5, 1142–1148 (November 1985). This essay indicates a preferred orientation of the tilting disc both in the aorta position and in the mitral position, providing corresponding effects on the volumes of flow in the sections of the flow channel cross-sections in the plane of the valve ring and upon the distal flow profile. This possibility is not provided in the case of bi-leaflet prosthetic valves of symmetrical structure or design.

As stated above, a bi-leaflet prosthesis, particularly a bi-leaflet prosthesis wherein both leaflets pivot on a common axis, provides certain advantages compared with a tilting disc prosthesis. However, in addition to the selection of size (valve ring diameter) it would be desirable to provide the surgeon with a further possibility to affect the flow conditions with such a bi-leaflet artificial valve.

SUMMARY OF THE INVENTION

Starting therefrom, an object of the invention is to solve the technical problem of providing a bi-leaflet prosthetic heart valve of the type indicated above, wherein both leaflets pivot on a common axis, that provides the surgeon an additional possibility to affect the flow conditions.

In order to solve the fore-mentioned technical problem, the present invention provides a bi-leaflet prosthetic heart valve, including an essentially circular valve ring, defining a circle and a valve ring plane, having an inner circumference, and defining a flow channel for the blood flow. An axle is secured to the valve ring and is arranged eccentrically, that is, parallel to and at a distance from a diameter to a circle. Two essentially half-moon-shaped leaflets both pivot independently of each other on the common axle. The leaflets are enabled, depending on the direction of the blood flow, to assume an open position, wherein both leaflets extend essentially at right angles to the valve ring plane and to assume a closed position, wherein both leaflets extend essentially in the direction of the valve ring plane, and virtually occlude the flow channel with their combined areas. One leaflet includes a greater area than the area of the other leaflet.

BRIEF DESCRIPTION OF THE DRAWINGS

In the following, a bi-leaflet prosthetic heart valve according to the present invention will be described in more detail with reference to preferred embodiments and to the accompanying drawings, wherein:

FIG. 7b is a plan view of the embodiment shown in FIG. 8a;

FIG. 8b is a plan view of the embodiment shown in FIG. 8a;

FIG. 9b is a further cross-sectional view of the embodiment shown in FIG. 9a.

Figure 1:
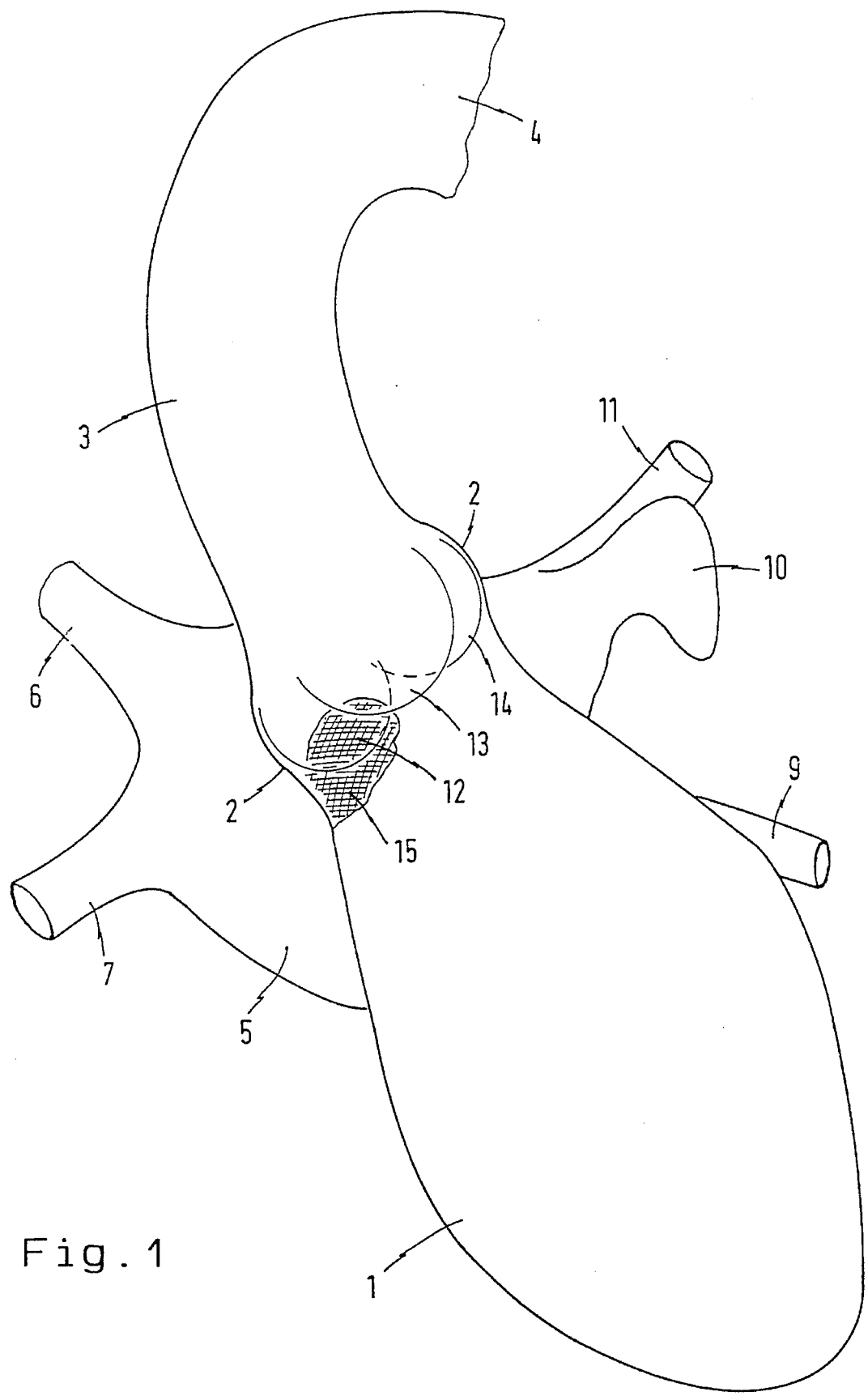
FIG. 1 is a simplified diagrammatic representation of the left heart cavity in the x-ray path, wherein sigmoids or valves of the natural aortic valve apparatus are indicated by heavy extended lines.

The drawings serve merely for illustration purposes and may not be construed to restrict the scope of the invention. The drawings show the artificial valve on a larger scale than in practice.

DETAILED DESCRIPTION OF THE INVENTION

Preferably, the leaflet comprising the larger area of a valve according to the present invention may occlude about 55% to 80% of the flow channel cross-section. The leaflet comprising the smaller area may occlude about 45% to 20% of the flow channel cross-section. If the leaflet of larger area occludes less than 55% of the flow channel cross section, then the effect achieved by the present invention is too small. If the leaflet of smaller area occludes less than 20% of the flow channel cross section, then, in this position distal to the heart valve, areas of recirculation and areas of reduced or raised flow may arise. Such flow areas enhance the formation of fibrotic and thrombotic material. As a result, there is a risk of an increased rate of thrombo-embolism.

According to an even more preferred embodiment of the present invention, the leaflet of larger area may occlude about 60% to 68% of the flow channel cross section and the leaflet of smaller area may occlude about 40% to 32% of the flow channel cross section. First of all, this even more preferred embodiment provides an asymmetrical distal flow profile suitable for adjustment to the given anatomical and physiological conditions. Secondly, this embodiment provides a safe, rapid and reliable closing action causing a reduced volume of regurgitation.

An asymmetrical bi-leaflet prosthesis according to the present invention may be used in any valve position. A heart valve according to the present invention may be preferably used in the aortic position or in the mitral position.

In case of an aortic prosthesis, the leaflet of larger area may occlude the dorsal portion of the flow channel cross section, and the leaflet of smaller area may occlude the ventral portion of the flow channel cross section. The opposite arrangement has been indicated by Bjork and Lindblom for a tilting disc prosthesis in the aortic position. This may be due to the fact that, in the open position, the tilting disc extends considerably beyond the valve ring plane. Contrary thereto, in the open position, the prosthesis according to the present invention comprises a reduced height and, thus, requires less clear space.

When arranging a prosthesis according to the present invention in the aortic position, it is possible to adjust the volume of blood in a better way to the anatomy of the aorta. In addition, damage to the endothelium is prevented.

When used as a mitral prosthesis, the leaflet of larger area is intended to occlude the dorsal portion of the flow channel cross section and the leaflet of smaller area is intended to occlude the ventral portion of the flow channel cross section. This type of arrangement enhances a scouring of the left ventricle.

The asymmetrical structure and arrangement of the leaflets provide, in the open position, a larger portion and a smaller portion of the flow channel cross section, through which the blood flows. Adjacent to the leaflet of larger area, a greater blood flow in terms of volume will occur and adjacent to the leaflet of smaller area, a smaller blood flow in terms of volume will occur. In addition, with the dimensions provided by the present invention, downstream of the smaller portion, a flow profile comprising a lower average flow velocity will build up than downstream of the larger portion. The surgeon is enabled to exploit this factor in adapting the asymmetrical flow profile to the physiology. This allows to reduce the risk of formation of turbulent flow zones and to reduce the size of dead water areas In addition, the endothelium at sections of the internal wall comprising sharp curves is preserved because lower blood flow velocities arise at such areas. The reduction of shearing stresses reduces or prevents hemolysis.

Obviously, the surgeon is provided with a further degree of freedom in order to influence the flow conditions occurring on the distal side of the heart valve by simply rotating the valve ring in the valve ring plane. In particular, such flow conditions may be better adapted to the anatomy and physiology of any individual case, thus reducing the risk of hemolysis.

European Patent document EP 0 079 844 B1, equivalent to U.S. Pat. No. 4,484,365 (Murguet et al.), discloses a heart valve comprising two leaflets having unequal areas. However, each leaflet pivots about its own axle secured to the valve/ring. Additionally, these two axles are not arranged in a common plane. This known arrangement necessarily requires two separate axles. The aim of this arrangement is to improve the valve opening action and, thus, to obtain very rapidly an entirely homogenous zone of blood flow. This known purpose cannot be realized by an asymmetrical flow profile as provided with the present invention.

In accordance with the present invention, an asymmetrical arrangement of the leaflets is obtained in such a manner that the axle is positioned eccentrically, that is, parallel to and at a distance from one diameter of a circle defined by the valve ring. In this case the axle, or more precisely, the longitudinal axis of the mechanically effective axle (shaft) forms a chord of this circle. The distance of the chord from a parallel diameter of this circle is designated as eccentricity. Preferably, the eccentricity, that is, the distance of a longitudinal axis of the axle to a parallel diameter, may comprise about 4% to 22% of the internal diameter of the valve ring. This magnitude of eccentricity provides the desired relationship between the leaflet comprising the larger area and the leaflet comprising the smaller area.

The axle comprises two opposite end portions. Each end portion is retained or supported in a shaft bearing formed in the valve ring. Preferably, the shaft bearings are formed like recesses or apertures passing through the valve ring.

According to a further advantageous embodiment, the shaft bearings are formed like longitudinal recesses supporting the end portions of the axle in a floating manner. That is, the end portions are free to move and/or to adjust in a limited range. A range of adjustment for the end portions of the axle within the longitudinal shaft bearings may amount about 2 to 4 mm. Preferably, a direction of the longitudinal shaft bearing recesses may extend from a point below the valve ring plane on the left side to a further point above the valve ring plane on the right side. This means that in a case of an aortic prosthesis, the longitudinal shaft bearing recess may extend from the caudal to the cranial direction and from the ventral to the dorsal direction. In case of a "floating" or movable shaft bearing, any pressure gradients within the blood flow are reduced and the action of opening and closing the leaflets is improved. The end portions of the axle and the space of the shaft bearing (recess) may comprise suited dimensions and configurations in order to guarantee a constant rinsing of the shaft bearing areas with fresh blood. In the area of the two shaft bearings, the valve ring may comprise sections of greater height (known as ears), in order to provide sufficient space for the longitudinal and inclined recesses of the shaft bearings.

According to a further advantageous embodiment, such a longitudinal shaft bearing, extending inclined to the direction of the blood flow, may be provided at a valve ring comprising on its inner circumference, at least in the area of the shaft bearing, a configuration or contour that becomes wider in the direction of the blood flow. This means that when the axle moves in the direction of the blood flow, the distance (gap or space) between the inner circumference of the valve ring and the adjacent edge section of the leaflet widens at the same time. More blood may flow through the gap, which increases or widens, respectively, between the edge of the leaflet and the inside of the valve ring. The improved blood flow reduces the risk of forming a thrombus, which is notoriously large with known bi-leaflet prostheses in the area of the attachment points.

According to a further preferred embodiment, the axle comprises a two-part structure, consisting of two axle portions. Each axle portion comprises at one end a thickened head portion, retained within a shaft bearing. At the other end, each axle portion comprises an opposite end portion, wherein one opposite end portion is formed like a socket. The other, opposite, end portion is formed like a pin, enabled to be inserted in the socket. In addition, where the pin and socket engage with each other, a locking system may be incorporated, for example in the form of a tongue and groove arrangement. A two-part structure of the axle provides for an easier manufacture and assembling of the prosthesis, because bending stresses are avoided that might result in mechanical stresses and hairline cracks, which would adversely affect the useful life of the prosthesis.

The shape of each leaflet is essentially like a half-moon, having one edge section that is curved and essentially semi-circular and one further edge section that is straight. The straight edge section is integrally formed with one or two sleeve portions, comprising bores through which the axle passes. In a first version, this sleeve portion starts at the outer end of the straight edge section and extends approximately as far as the center of the leaflet. Both leaflets are arranged parallel to, and opposite with each other in such a way as to provide an alignment of the two bores of the sleeve portions. The axle is passed through the aligned bores.

In a second version, preferred when using leaflets of larger area, two sleeve portions may be integrally formed with the straight edge section, thus providing a gap between the sleeve portions. A further sleeve portion is integrally formed with the straight edge section of the other leaflet, preferably the leaflet comprising the smaller area. This further sleeve portion fits into the gap between the other two sleeve portions.

Following an assembling of the two leaflets, all the sleeve portions provide an aligned bore, and the axle may be passed through the aligned bore. By means of these sleeve portions, the two leaflets pivot, like a hinge on a single axle or shaft. This hinge-like linkage provides a safe and reliable attachment of the two leaflets to the valve ring.

Preferably, the external diameter of the axle and the internal diameter of the bore(s) in the sleeve portions are selected and matched in such a manner that, first, the leaflets pivot easily around the axle and, secondly, the blood is essentially hindered to enter the bores in the sleeve portions. To this end, the surfaces may be ground to a precision of a few micrometers. An access of the blood to the surface between the axle and the inside of the sleeve portion is prevented. Consequently, any damage to components of the blood, including the formation of clots, is reduced to a minimum. Further, dead water areas are prevents, which frequently form the point of origin for the formation of a clot in other known valves.

The leading faces of the sleeve portions are aligned vertically to the axle. This ensures that each leaflet may pivot around the axle independently of the other leaflet.

The leaflets are made of rigid material and comprise a typical wall thickness of between about 0.5 mm and 2 mm in the area of the wing-like occluder. The wall thickness may increase when proceeding towards the sleeve portion, so that the surface of the leaflet facing the blood flow, in particular, provides a tangent-like and continuous transition in the curvature of the sleeve portion. In addition, and according to a preferred embodiment, the surface of the leaflet facing the blood flow may be provided with a convex contour or configuration. This provides a smooth configuration offering little resistance to the blood flow.

A convex contour of the surfaces facing the flow reduces any tension of the stagnation zone on the distal side of the leaflets arranged in an open position in a V-shaped manner. Those surfaces essentially in contact with the blood stream are lightly curved or arched and, due to their arrangement and configuration, are optimally adapted to the blood flow. All surfaces are constantly being rinsed with blood; there are no dead water areas. There are no edges and recesses which might cause a turbulent flow of the blood stream and might cause a deposition of fibrinogen. Consequently, a reduced rate of thrombo-embolism is to be expected.

When in the closed position, the leaflets are arranged essentially in the plane of the valve ring. One or more stops may be provided on the inner circumference of the valve ring, which prevent the leaflets from oscillating through the plane of the valve in the caudal direction, for example, in the aortic position. As an example, such stops may be formed like step sections running round the inside of the valve ring, and providing a limit stop upon which the semi-circular edge section of the leaflet may rest.

Preferably, the step sections extend along a limited area of the inner circumference of the valve ring. Preferably, the step sections extend on both sides of each shaft bearing. For example, each step section may comprise a length of only about 3 mm to 6 mm. Such step sections may be formed integrally and smooth with the inner circumference wall of the valve ring. In this area only a low relative velocity of the edges of the moved leaflets arises in relation to the fixed step sections. This avoids cavitation, which might result in erosion of the edges of the leaflets. In addition, the section of leaflet edge in contact with the step sections is minimized.

When in the open position, the leaflets assume an arrangement that is essentially parallel to and in the direction of the blood stream. Essentially, the leaflets take up a V-shaped position, defined by a leaflet aperture angle. The leaflet aperture angle is determined and defined by two straight lines, starting at the longitudinal central axis of the axle and passing through the two crown points of the semi-circular leaflets.

In the case of an in vitro simulation of the aortic position, and using the aforementioned test method of V. N. Yurechko to provide a visible demonstration of the flow conditions in this open position, essentially three different flow zones could be observed. In each case, a turbulent flow is found in the bulbs of the aorta (sinus). Further, each a flow zone is found on each side of the two leaflets. A stagnation zone is found distal to the V-type arranged leaflets. The size of this stagnation zone is essentially proportional to the leaflet aperture angle. First, the stagnation zone should be kept as small as possible. Secondly, if the leaflet aperture angle is too small, then uncertainties and delays may arise in the response of the leaflets to a reversal of the direction of blood flow, which ultimately results in a renewed assuming of the closed position.

According to a preferred embodiment, the leaflets pivoting on a common axle may assume in the open position a leaflet aperture angle of about 10° to 40°. If the leaflet aperture angle is less, then the response of the leaflets to a reversal in direction of blood flow is unsatisfactory. If the leaflet aperture angle is larger, then an excessive extension of the stagnation zone may be observed. Even more preferred is a leaflet aperture angle of about 12° to 18°, because this provides a particularly small stagnation zone and a safe and reliable closing action.

According to another preferred embodiment, the internal circumference of the valve ring may comprise stops, which prevent the leaflets from oscillating beyond the intended position in their open position. As an example, such stops may be formed like pins that project inward from the upper section of the valve ring and are located between the two leaflets when they assume their open position. It should be noted that, when in the open position, the leaflets do not necessarily have to assume a symmetrical position adjacent to a vertical plane on the valve ring plane. Rather, each leaflet may assume a position in the open position that corresponds essentially to the flow lines of the blood stream.

According to another preferred embodiment, the valve ring comprises at least one section having a larger height than other valve ring sections. Preferably, the valve ring section of larger height may be arranged adjacent to the leaflet of smaller area. In addition, the valve ring section of larger height may be curved slightly inward. This improves the inflow of blood into the adjacent curved wall section of a heart chamber or vessel.

Both, the valve ring and the two leaflets are made of a durable, biocompatible material, comprising a surface that prevents blood coagulation. A preferred material for the surfaces is pyroluric carbon (polycarbon). Typically, the valve ring and/or the leaflet comprise stiffening or strengthening intermediate layers that are coated with pyrolytic carbon. As an example, the inner layers can be composed of high grade steel, titanium, an alloy of aluminum and titanium, an alloy of cobalt, such as HAYNES 25, or other known suitable materials.

A material which is particularly preferred may be obtained by sputtering a titanium target with carbon. This provides a multi-layered structure, comprising an outer layer of pyroluric carbon bonded to a core of metallic titanium via one or more intermediate layer(s) of titanium carbide(s). Adhesion and durability of the outer layer of pyroluric carbon is particularly good.

Typically, the valve may comprise a height of between 3 mm and 6 mm, and may comprise a flow channel diameter, depending upon the application and age of the patient, of between about 12 mm and 29 mm. The leaflets comprise adapted dimensions in order to virtually occlude with their combined areas the flow channel defined by the valve ring. There should be provided a slight flow of blood even when the leaflets assume their closed position.

Preferably, the internal circumference of the valve ring comprises a convex shape or contour. Alternatively, the internal circumference of the valve ring may widen continuously in the direction of blood flow.

A groove may be provided a round the external circumference of the valve ring in order to insert a suture ring of known configuration into the groove, thus enabling the artificial valve to be attached to the heart tissue. Typically, the suture ring consists of a plastic thread or strip inserted into the groove on the valve ring. Preferably, the suture ring may be made of "Dacron", and a fabric that projects above the groove may be made of plastic, preferably "Teflon" fibers. According to another preferred aspect, the suture ring may comprise an orientation mark, which automatically indicates to the surgeon which is the leaflet of greater area and which is the leaflet of smaller area. As an example, this orientation mark may comprise a specified coloring, a removable flag or the like.

According to another preferred embodiment, the valve ring may be held rotatably within the suture ring, following the attachment of the suture ring to the tissue. This arrangement may be used for a fine calibration of the prosthesis, once the suture ring is attached to the tissue. In this case, it is necessary to provide for a certain degree of force to rotate the valve ring, in order to prevent unintentional rotation of the valve ring.

FIG. 1 shows in a simplified diagrammatic representation the left side heart cavities in the x-ray path according to Frank H. Metter "Farbatlanten der Medizin, The Ciba Collection of Medical Illustrations", volume 1; Heart, page 28, 3rd edition, 1990, Georg Thieme Verlag, Stuttgart-New York. In detail, FIG. 1 shows the left ventricle 1, the bulbs 2 of the aorta, the aorta ascendens 3 and the aortal arch 4. In the background, there are the left side atrium 5 including V. pulmonalis sup. dext. 6, V. pulmonalis 7 and V. pulmonalis inf. sin. 9, as well as the left side auricular appendix 10 with V. pulmonalis sup. sin. 11.

Within the bulbs 2 of the aorta there are the sigmoids or valves of the aortic valve apparatus. The sigmoids or valves comprise the rear sigmoid valve 12, the left sigmoid valve 13 and the right sigmoid valve 14, indicated diagrammatically by semi-circular curves. The membranous septum 15 is indicated by hatching.

Figure 2:
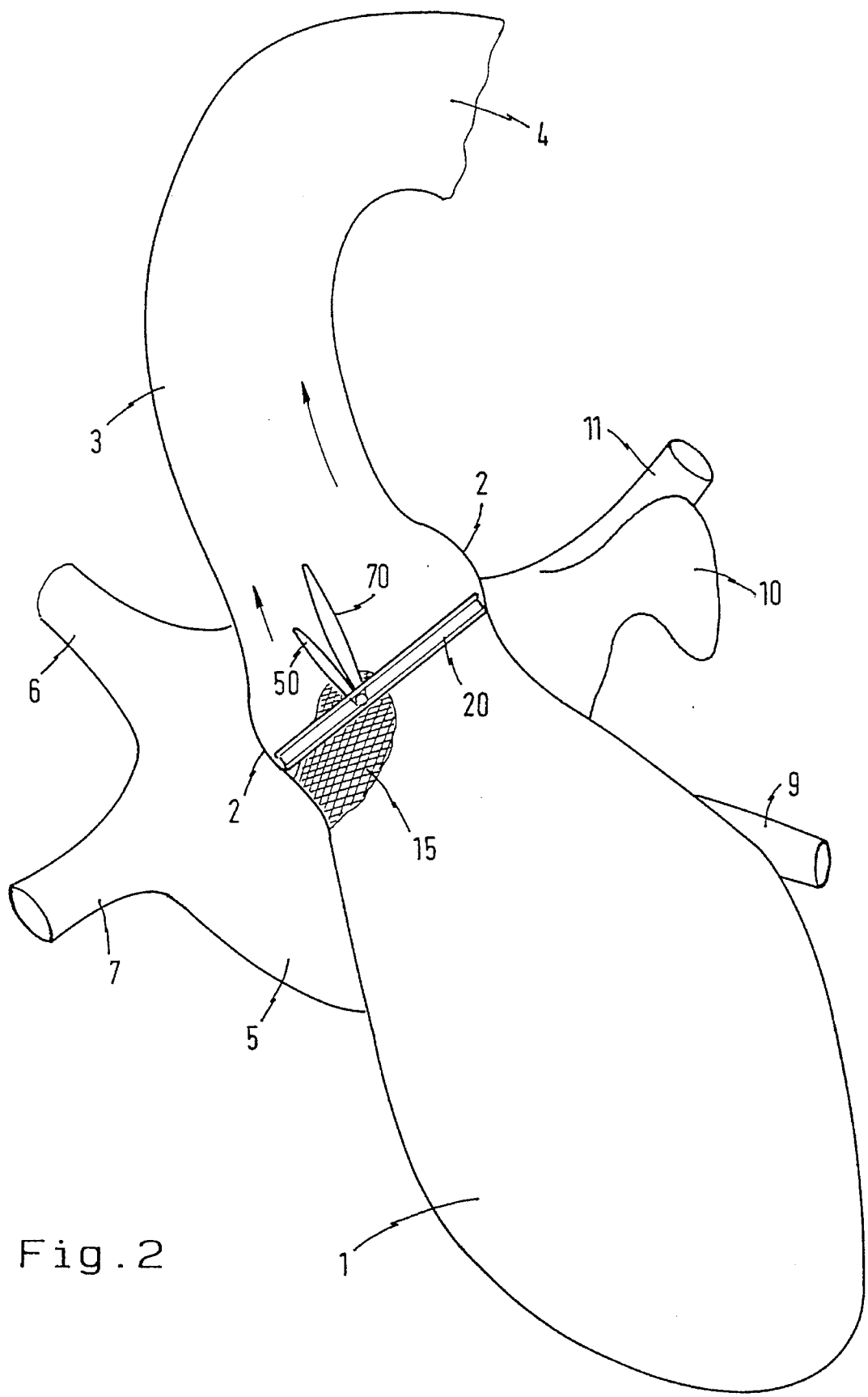
FIG. 2 is a representation similar to FIG. 1, but including a prosthesis according to the present invention in the aortal position.

According to FIG. 2, the sigmoid valves of the natural aortic valve apparatus are replaced by an artificial valve according to the present invention. When the aortic valve is replaced, the diseased valve sigmoids are excised; in addition, calcium deposits bridging the valve ring and present within the outflow path of the left ventricle are removed. However, a small portion of the natural valve is left by the wall of the aorta, and the suture ring of the artificial valve is sewn firmly thereto. Particular care must be taken in order to arrange the upper edge of the artificial valve well below the coronary ostia. In addition, any obstruction of the mitral valve sigmoid has to be avoided. This provides limitations when replacing valves in the aortic position.

Figure 3:
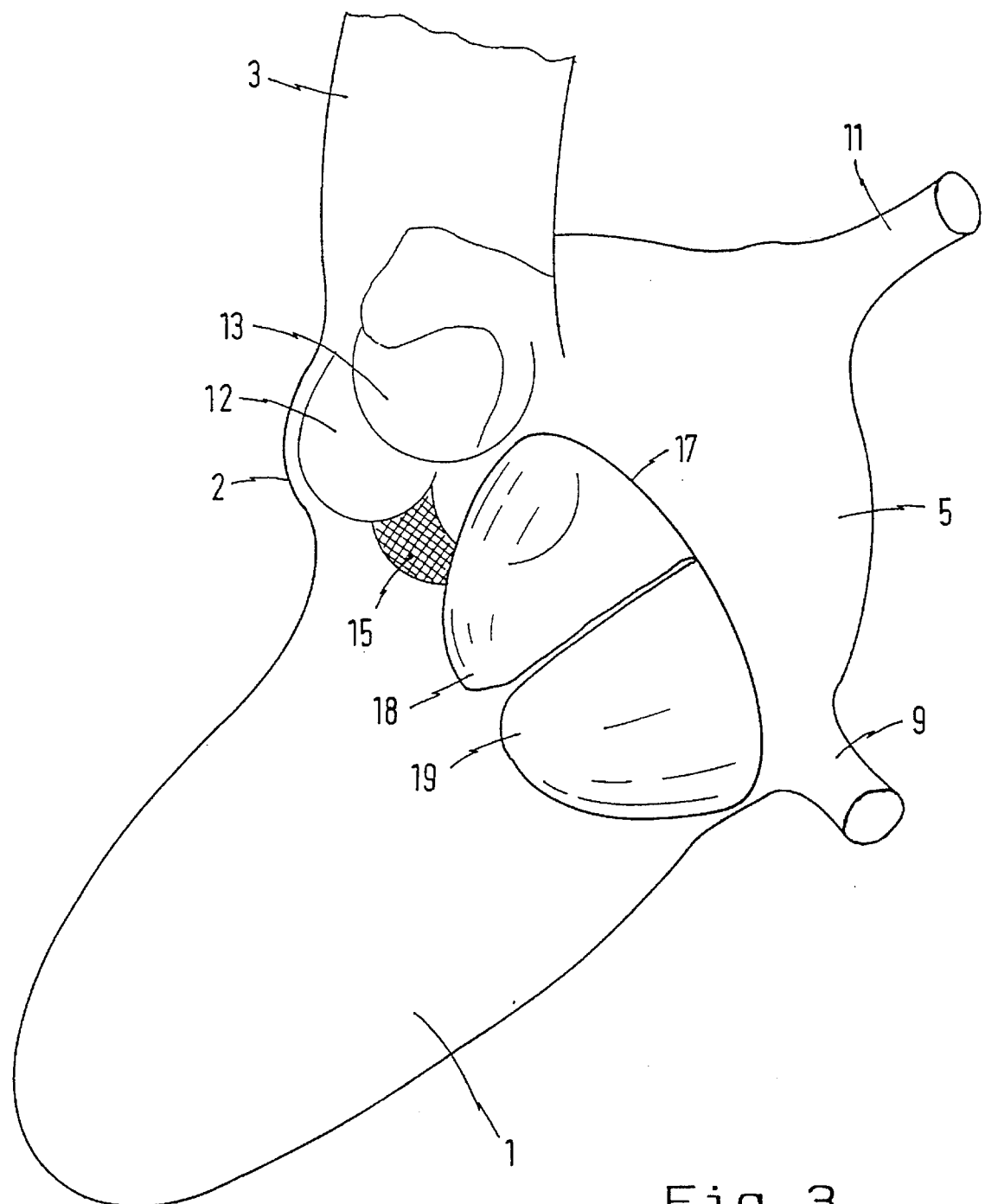
FIG. 3 is a simplified diagrammatic representation of the left side heart cavities in the lateral x-ray path, wherein in addition the valve ring and the two main sigmoids or valves of the natural mitral valve apparatus are indicated.

FIG. 3 shows in a simplified diagrammatic representation of the left side heart cavities in the lateral x-ray path according to Frank H. Metter, "Farbatlanten der Medizin, The Ciba Collection of Medical Illustrations", volume 1; Heart, page 29, 3rd edition, 1990, Georg Thieme Verlag, Stuttgart-New York, including the components already explained above. In addition, the left atrium 5 and the mitral valve apparatus including mitral valve ring 17, the front sigmoid 18 and the rear sigmoid 19 are indicated.

Figure 4:
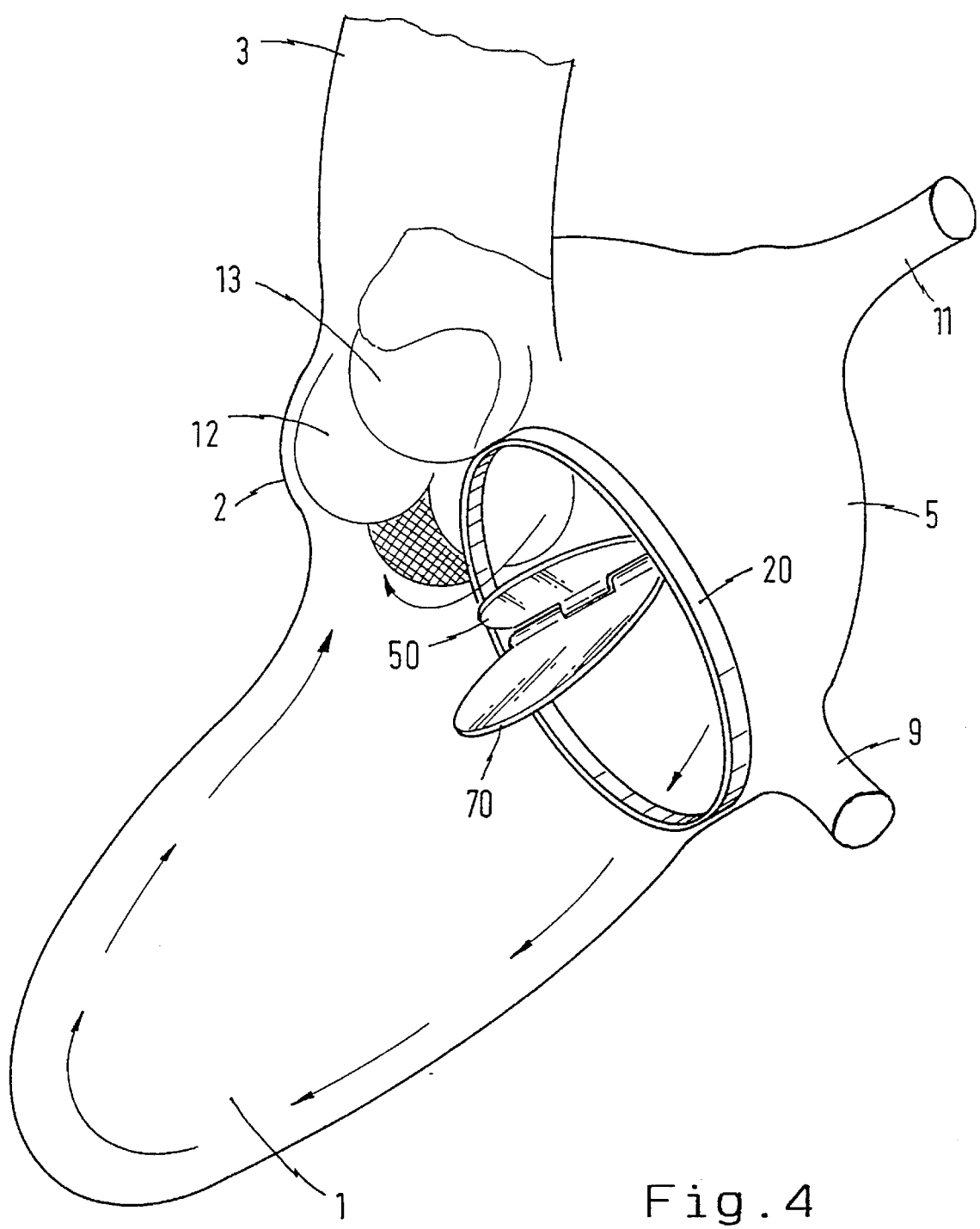
FIG. 4 is a representation similar to FIG. 3, but including a prosthesis according to the present invention in the mitral position.

According to FIG. 4, the sigmoids of the mitral valve are replaced by an artificial valve according to the present invention. Frequently, when replacing the mitral valve, the papillary muscles are cut in two, and the sigmoids are excised with the tendinous fibers and the stumps of the muscles. The suture ring of the artificial valve is sewn onto the mitral valve ring. There is a particular risk of damage or obstruction of an aortic valve sigmoid. In addition, the blood stream created when the aortic valve sigmoid is closed (aortal regurgitation) may delay the closing action of the leaflet in the mitral position.

According to FIGS. 2 and 4, the leaflets assume an open position. It is easy to be seen that the asymmetrical arrangement of the leaflets in this position obviously creates a flow profile that is better suited to match the anatomy and physiology of the heart than a symmetrical arrangement of the two leaflets.

Figure 5:
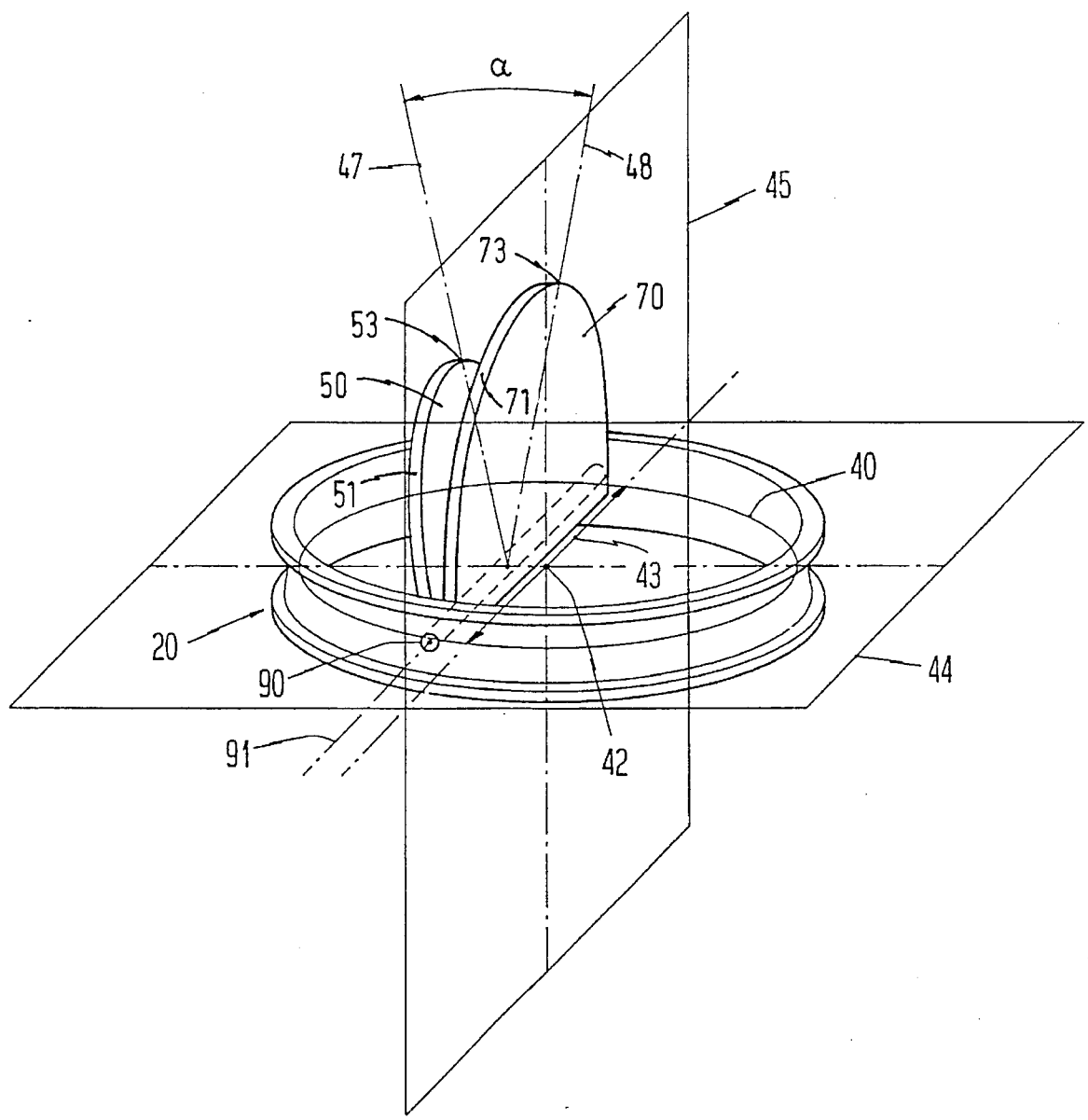
FIG. 5 is a diagrammatic view showing a bi-leaflet prosthetic heart valve according to the present invention in order to illustrate and explain definitions.

Referring to FIG. 5, various definitions used within the frame of the present documents are explained. The valve ring 20 defines a corresponding circle 40, comprising a center point 42. The circle 40 extends, within and, thus, defines a valve ring plane 44. A standard central plane 45 to the valve ring plane 44 extends vertically to the valve ring plane 44 and includes the center point 42 of the circle 40. In addition, the circle 40 comprises a diameter 43, extending within the standard central plane 45. The asymmetrical arrangement of the leaflets 50 and 70 according to the present invention is characterized by the fact that a longitudinal central axis 91 of the axle (shaft) 90, on which both the leaflets 50 and 70 pivot, extends at a distance from the standard central plane 45 or diameter 43. Expressed in other words, the axle 90 is aligned in parallel with and at a distance from a diameter of the circle 40 defined by the valve ring 20. The axle is thereby arranged eccentrically or asymmetrically with respect to the standard central plane 45 on the valve ring plane 44.

Moreover, a leaflet aperture angle ($\alpha$) is defined by two straight lines 47 and 48, which cut the longitudinal central axis 91 of the axle 90 and pass through the crown point 53 of the first leaflet 50 or pass through the crown point 73 of the second leaflet 70.

The significant components of the prostheses as depicted in more detail in FIGS. 6a to 9c include a valve ring 20 and the two leaflets 50 and 70, as well as an axle 90.

Figure 9A:
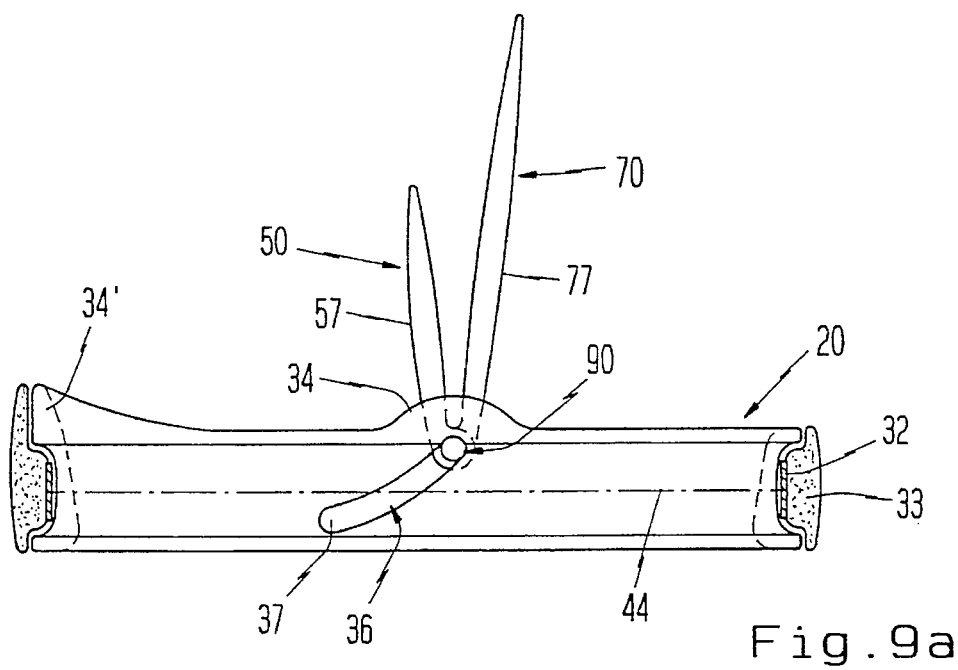
FIG. 9a is a cross-sectional view of a further additional embodiment of a prosthesis according to the present invention.

Typically, the valve ring 20 is circular in form and, as a rule, is of constant height. Alternatively, one side of the valve ring 20 adjacent to the leaflet 50 of smaller area may comprise greater height, section 34' of valve ring 20, as shown in FIGS. 9a and 9c. In addition, in the area of the "ears" 34, shown in FIGS. 9a and 9c, the valve ring 20 may comprise a section of greater height, in order to provide sufficient space for extended, longitudinal, inclined shaft bearings 36.

Figure 6A:
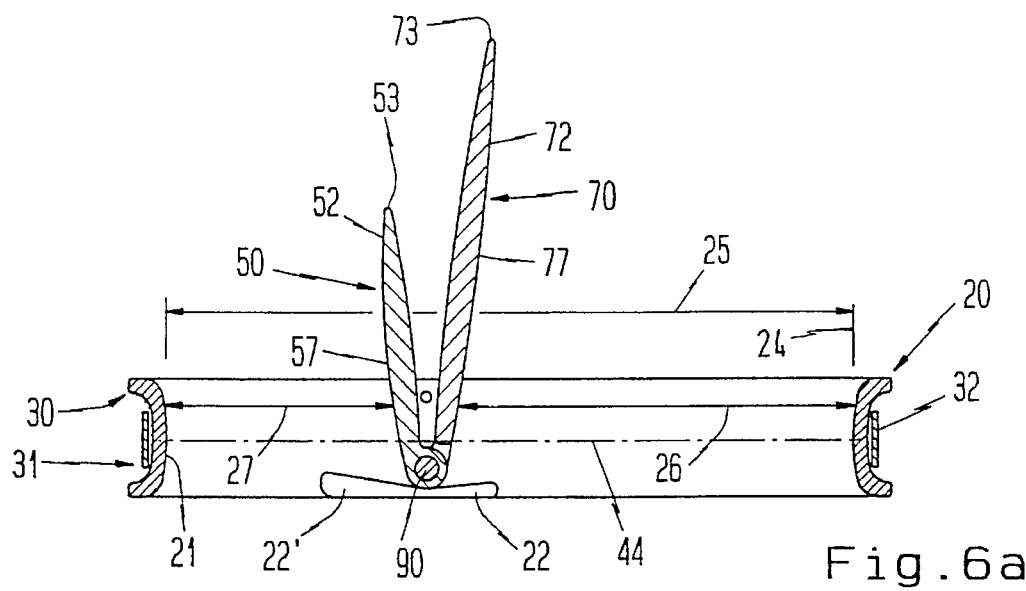
FIG. 6a is a cross-sectional view of a prosthesis according to a first embodiment of the present invention, wherein the leaflets assume an open position.

As can be seen in FIG. 6a, the valve ring 20 comprises an internal circumference 21, defining a flow channel 24 for the blood flow. The direction of blood flow that moves the leaflets 50 and 70 from the closed position to the open position is indicated by the arrows A. The flow channel 24 comprises a flow channel cross-section 25, extending within the valve ring plane 44.

According to the asymmetrical arrangement of the leaflets 50 and 70, the flow channel cross-section 25 includes a larger section 26 and a smaller section 27. In the aortal position the larger section 26 is located on the dorsal side and the smaller section 27 is located on the ventral side. In the mitral position, the larger section 26 is located on the dorsal side and the smaller section 27 is located on the ventral side. Preferably, the internal circumference 21 comprises a convex curvature.

In addition, the valve ring 20 comprises an external circumference 30, including a circumferential groove 31 and a strip 32 or plastic thread, preferably "Dacron," being inserted into the groove 31. A suture ring is attached in known manner to the strip 32. By means of the suture ring, the artificial valve may be attached to the natural tissue. Examples of a suture ring 33 are indicated diagrammatically in FIGS. 9a, 9b and 9c.

Each leaflet 50 and 70 comprises an essentially half-moon-shaped circumference or outline 51 and 71, respectively. The outline includes a curved or semi-circular edge section 52 and 72, respectively, and a straight edge section 54 and 74, respectively. At a distance on the distal side from the straight edge sections 54 and 74, each curved edged section 52 and 72 comprises a crown point 53 and 73. The outlines 51 and 71 encircle or define an area 55 and 75, respectively, of each leaflet 50 and 70, respectively, extending within the plane of the leaflet.

When arranged essentially adjacent to each other in V-shape, each leaflet 50 and 70 has an internal or proximal face 56 or 76, respectively, and an external or distal face, which is hereinafter designated the side 57 or 77, respectively, facing the flow. The internal faces 56 and 76 and the sides 57 and 77 facing the flow define each a section profile of the leaflet 50 or 70, respectively, that may be described by what is known as a skeleton line.

Within the present invention, there is no special limitation of the section profile of the leaflets 50 and 70. The section profile may comprise various forms, including a straight, even configuration; a convex configuration; a concave configuration; or, when proceeding from the crown point 53 or 73 to the straight edge 54 or 74, a combination of such configurations. Examples of the combined configurations for the inner faces 56 and 76 and the side 57 and 77 facing the flow of the leaflets 50 and 70, respectively, are described in patent documents WO 90/08519 or EP 0 277 527 A1. Within the present invention, the side 77 facing the flow or the inner face 76 of the leaflet 70 of larger area may comprise a configuration that differs from the configuration of the side 57 facing the flow or the inner face 56 of the leaflet 50 of smaller area. As an example, the differences between the various forms of configuration may be less marked in the leaflet 50 of smaller area.

The leaflets 50 and 70, previously explained, are arranged to pivot in such a manner that each leaflet is enabled to assume its intended position in the opened position or in the closed position independently of the other leaflet, merely under the action of pressure and direction of the blood flow. The pivoting attachment of the leaflets 50 and 70 to the valve ring 20 is achieved indirectly via an axle 90, on which the two leaflets 50 and 70 pivot. This axle 90 is supported in the valve ring 20 either rotatably or in a fixed manner.

Figure 6B:
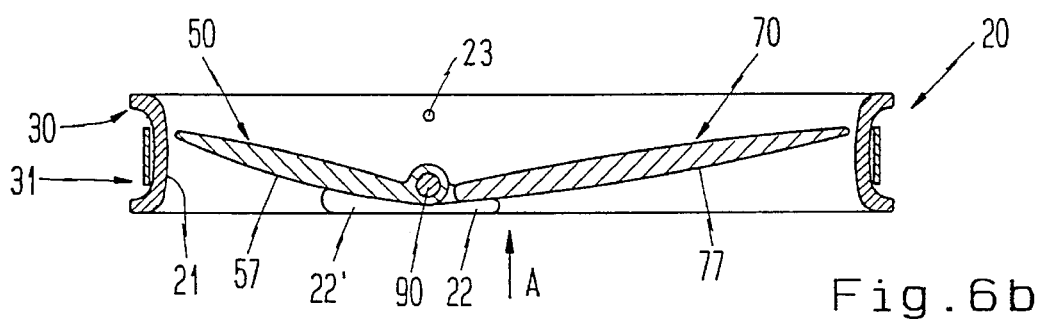
FIG. 6b is a representation similar to FIG. 6a, but wherein the leaflets assume a closed position.
Figure 6C:
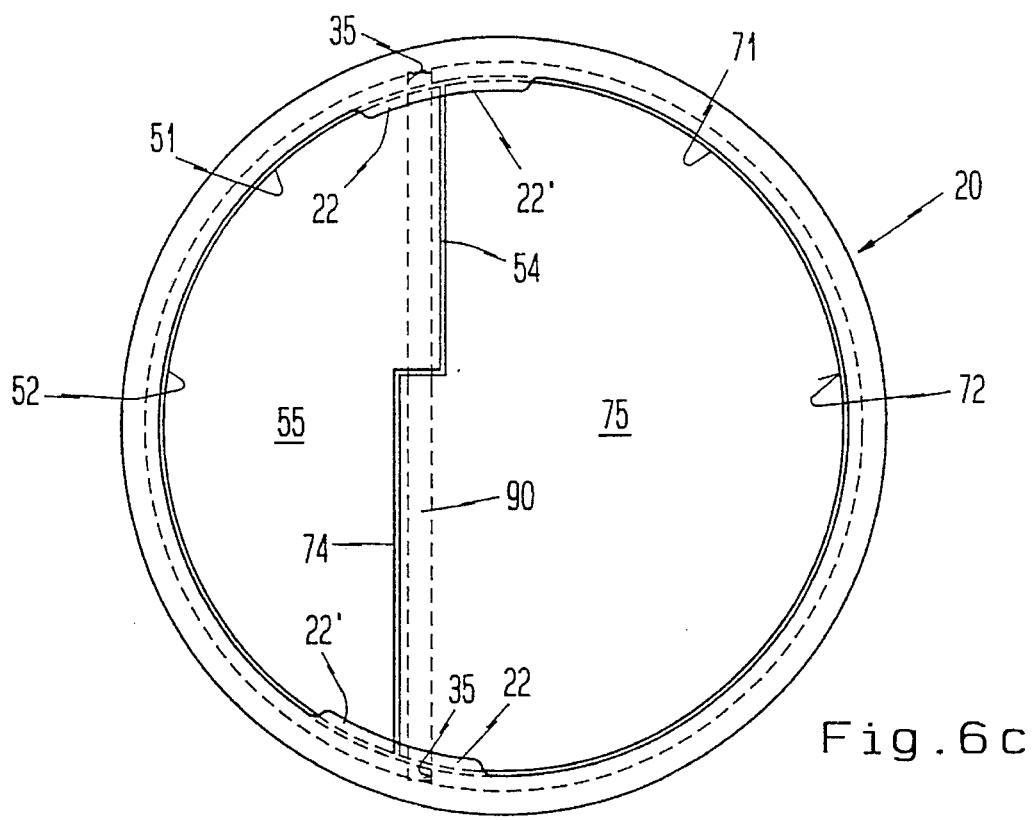
FIG. 6c is a plan view from below, in the direction of flow, of the prosthesis shown in FIG. 6b.

FIGS. 6a, 6b and 6c illustrate a first embodiment of a prosthesis according to the present invention. The leaflet 70 comprises a larger area 75 than the area 55 of the leaflet 50. Both leaflets 50 and 70 are attached to the common axle or shaft 90 and both leaflets 50 and 70 are enabled to pivot independently of each other. The axle 90 is retained in recesses 35 on the valve ring 20. This axle 90 has a longitudinal central axis 91 that is arranged eccentrically, that is, parallel to and at a distance from a diameter 43 of the circle 40, as defined by the valve ring 20, as shown in FIG. 5.

Several step sections 22 and 22' of gentle and rounded nature are formed on the internal circumference 21 of the valve ring 20. The step sections 22 and 22' provide stops preventing the leaflets 50 and 70 from oscillating beyond their intended position in the closed position. As depicted, a section of step 22 or 22' extends on both sides of the shaft bearing 35 on the internal circumference 21 of the valve ring 20.

Moreover, projections 23 are formed on the internal circumference 21. The projections 23 provide stops, preventing the leaflets 50 and 70 from oscillating beyond their intended position in the open position. In this embodiment each leaflet 50 and 70 comprises a convex configuration on the side 57 and 77, respectively, facing the blood flow.

Figure 7A:
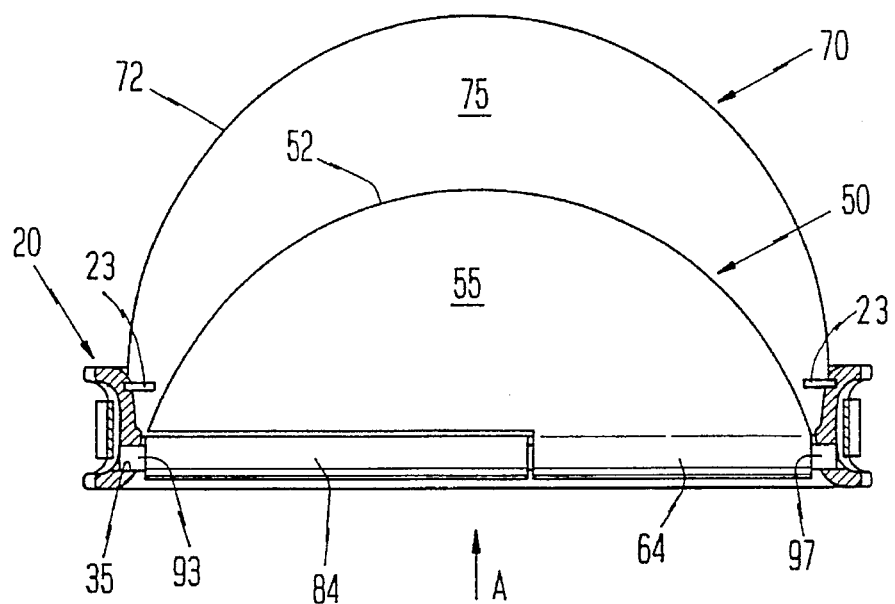
FIG. 7a is a side view of another embodiment of a prosthesis according to the present invention.
Figure 7B:
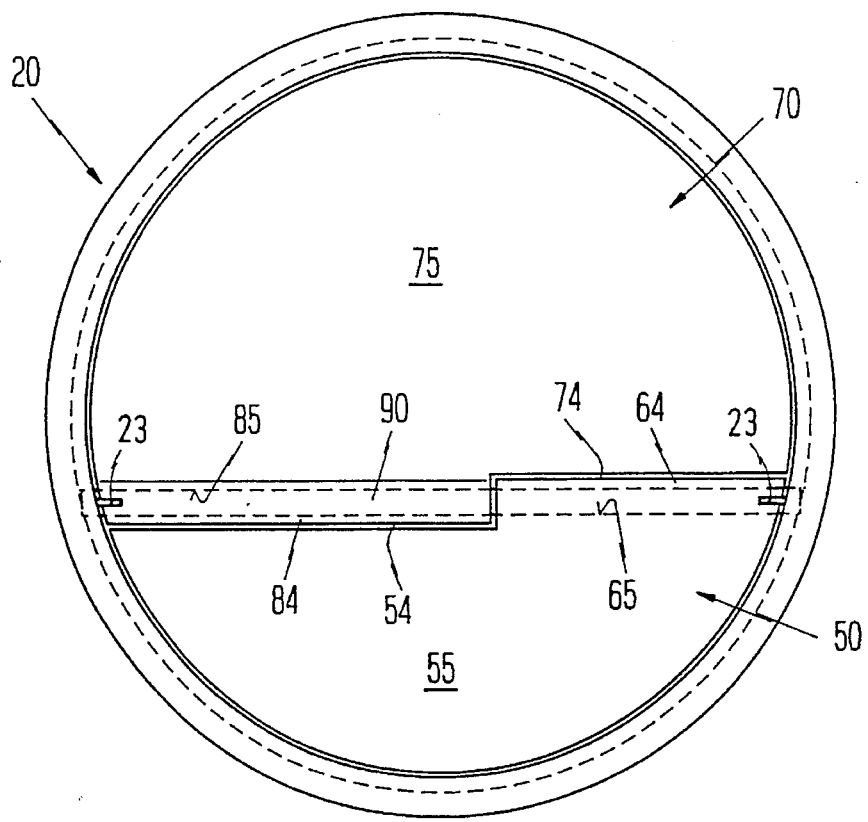

FIGS. 7a and 7b depict a first version of a pivoting arrangement of the leaflets 50 and 70 on the axle 90 for the prosthesis according to FIGS. 6a to 6c. In this embodiment a sleeve portion 64 or 84 is integrally formed with the straight edge section 54 or 74, respectively, of each leaflet 50 or 70, respectively. Each sleeve portion 64 or 84 starts at the curved edge 52 or 72, respectively, and extends approximately as far as the center of the leaflet. Next to this, the edge of the leaflet is cut away in order to provide space for the portion of the sleeve on the other leaflet.

On the leaflet 70 of larger area, the sleeve portion 84 may comprise a greater length that the sleeve portion 64 on the leaflet 50 of smaller area. Each sleeve portion 64 and 84 comprises a continuous bore 65 and 85, respectively. If the two leaflets 50 and 70 are fitted together, these two bores 65 and 85, respectively, are in alignment with each other, and the axle 90 may extend through the aligned bores 65 and 85. The axle 90 comprises opposite end portions 93 and 97 oppositely projecting beyond the aligned bore 65 or 85 and are each retained in a shaft bearing 35 on the valve ring 20. In this embodiment the shaft bearings 35 are in the form of continuous round holes in the valve ring 20.

Figure 8A:
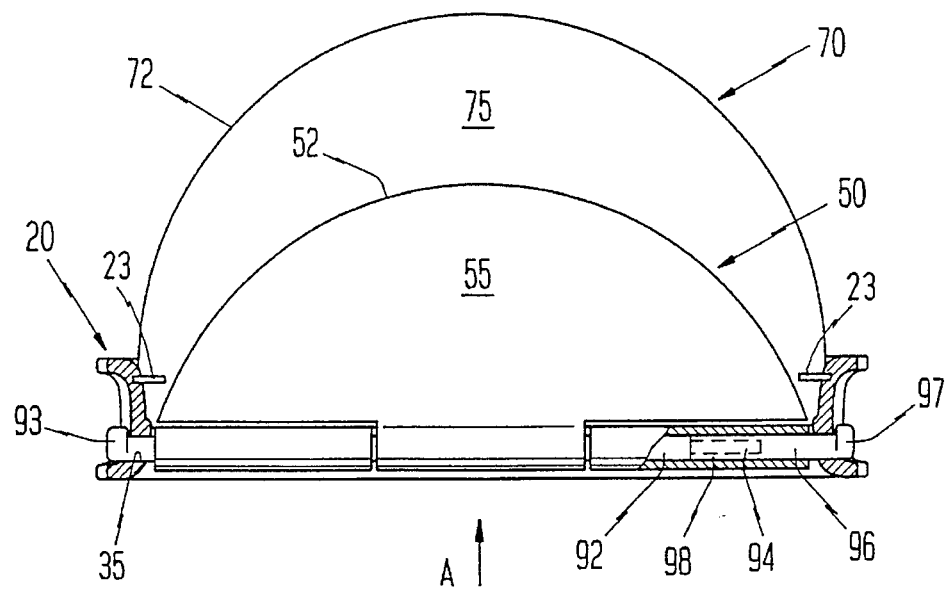
FIG. 8a is a side view of a further embodiment of a prosthesis according to the present invention.
Figure 8B:
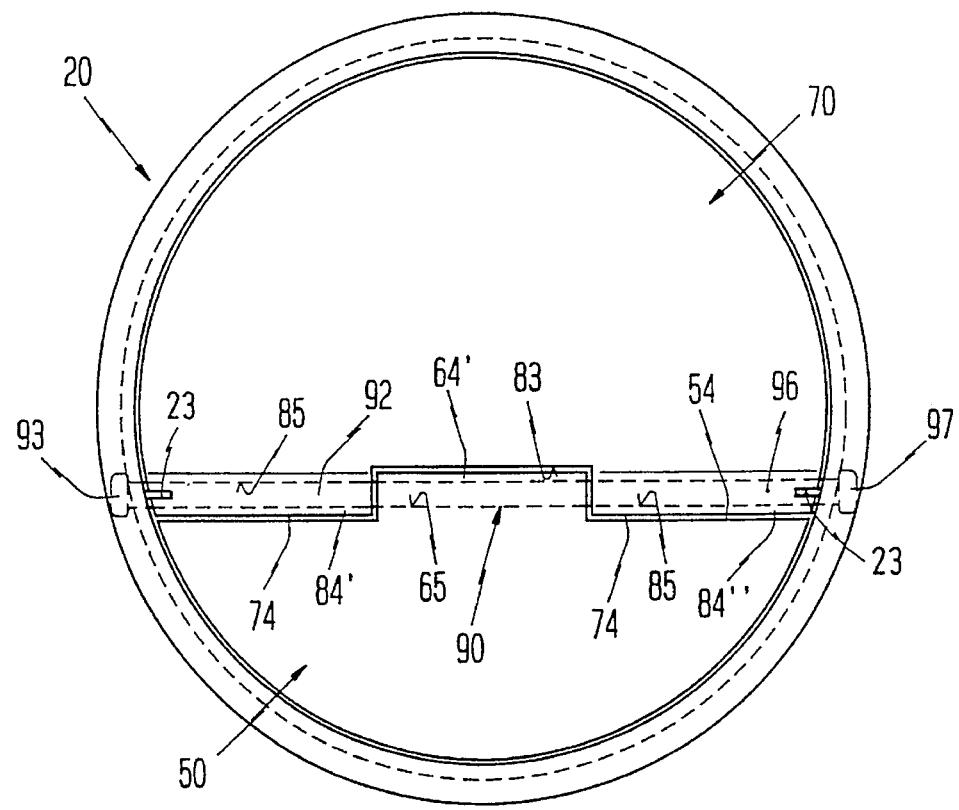

FIGS. 8a and 8b depict a second version of the pivoting attachment of the leaflets 50 and 70 on the axle 90 for the prosthesis according to FIGS. 6a to 6c. In this embodiment, the leaflet 70 of larger area comprises two sleeve portions 84' and 84", integrally formed with the straight edge section 74. These sleeve portions 84' and 84" extend inward from the curved edge section 72 and leave a gap 83 clear. Into this gap 83, projects a suitable sleeve portion 64', integrally formed with the straight edge section 54 of the leaflet 50 of smaller area. Each sleeve portion 64', 84' and 84" comprises a continuous bore 65 or 85. Following a fitting of the leaflets 50 and 70 these bores 65 and 85 are in alignment with each other. Now, the axle may extend through the aligned bores 65 and 85.

In this embodiment the axle comprises a two-part structure consisting of two axle portions 92 and 96. Each axle portion 92 and 96 comprises at one end a thickened head portion 93 or 97, respectively. The other end portions are formed like a socket 98 and like a pin 94, enabled to be inserted in the socket 98. Each thickened head portion 93 and 97 is retained in a suitable recess 35 on the valve ring 20.

Figure 9B:
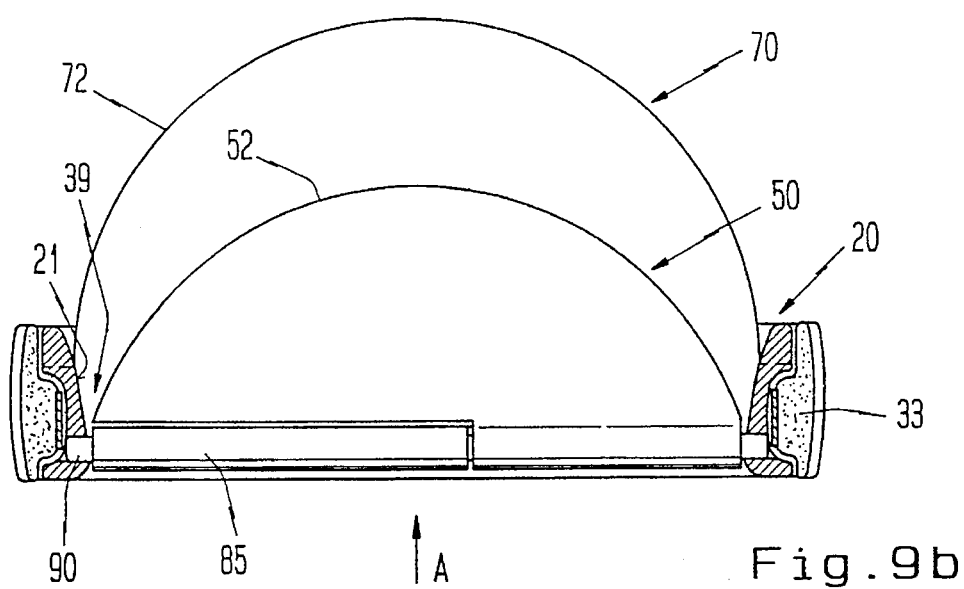
Figure 9C:
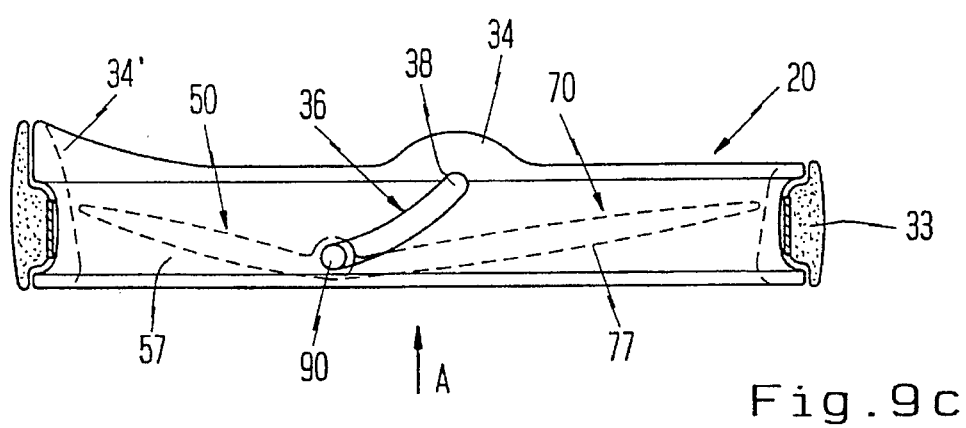
FIG. 9c is a plan view of the prosthesis shown in FIG. 9a and FIG. 9b, including extended, longitudinal, and inclined shaft bearings.

FIGS. 9a, 9b and 9c depict a second embodiment of a prosthesis according to the present invention. Once again, both leaflets 50 and 70 pivot on a common axle 90, the end portions 93 and 97 thereof are retained, in each case, in a shaft bearing. In this embodiment, each shaft bearing comprises the form of a longitudinal recess 36 extending in an inclined direction with respect to the valve ring plane 44.

As depicted in FIGS. 9a, 9b and 9c, this longitudinal bearing recess 36 extends from a point on the left side below the valve ring plane 44 to a point on the right side above the valve ring plane 44. With this arrangement, the longitudinal shaft bearing 36 has a bottom end portion 37 and a top end portion 38. In each case, the dimensions are selected in such a manner that the end portions 93 and 97 of the axle 90 are movably retained. That means that the end portions 93 and 97 are "floating" in this longitudinal shaft bearing 36.

In the closed position, the axle 90 will assume a position in the lower end portion 37. Under the pressure of the flowing blood, the leaflets 50 and 70 pivot into their open position. At the same time, the shaft 90 is enabled to move in the upper portion 38 of the longitudinal shaft bearing 36. In this way, the pressure gradient may be reduced and the loss of energy is also reduced.

As depicted, in the area of the expanded longitudinal inclined shaft bearing 36, the valve ring 20 is provided with what is known as ears 34. The ears 34 comprise a section of greater height than other valve ring sections.

As shown in FIG. 9b, this embodiment of a valve ring 20 comprises on its internal circumference 21 a contour or configuration that continuously becomes wider in the direction of the blood flow, indicated by arrow "A." When the axle 90 is situated in the lower end portion 37 of the longitudinal shaft bearing 36, a certain gap 39 exists between the face of the sleeve portion 85 with the adjacent curved edge 72 and the internal circumference 21 of the valve ring 20. When the shaft 90 moves into the upper end portion 38 of the longitudinal shaft bearing 36 in course of the opening action, this gap 39 increases. This improves the rinsing of this bearing zone with fresh blood.

In addition, as depicted in FIG. 9a, a valve ring portion 34' of greater height may be provided adjacent to the leaflet 50 of smaller area.

I claim:

1. A bi-leaflet prosthetic heart valve, comprising:

a substantially circular valve ring having an inner circumference defining a flow channel for blood flow;

an axle secured to said valve ring, said axle being parallel to but not co-linear with a diameter of said valve ring;

two substantially half-moon shaped leaflets hingedly connected to said axle and pivoting independently of each other, said leaflets having different cross-sectional areas, said leaflets moving between a closed position wherein the leaflets both are substantially in a plane of said valve ring and substantially occlude a flow of blood through said flow channel, and an open position wherein each of said leaflets are pivoted about said axle with respect to said closed position thereby permitting blood to flow through said flow channel.

2. A bi-leaflet prosthetic heart valve according to claim 1, wherein said axle is located a distance from a diameter of said valve ring that is about 4 to about 22 percent of a length of said diameter.

3. A bi-leaflet prosthetic heart valve according to claim 1, wherein in said closed position one of said leaflets having a larger cross-sectional area occludes from about 55 to about 80 percent of a cross-sectional area of said flow channel and a smaller one of said leaflets occludes from about 20 to about 45 percent of said cross-sectional area of said flow channel.

4. A bi-leaflet prosthetic heart valve according to claim 1, wherein in said closed position one of said leaflets having a larger cross-sectional area occludes from about 60 to about 68 percent of a cross-sectional area of said flow channel and a smaller one of said leaflets occludes from about 32 to about 40 percent of said cross-sectional area of said flow channel.

5. A bi-leaflet prosthetic heart valve according to claim 1, wherein said flow channel includes a larger dorsal section and a smaller ventral section, wherein said valve is adapted for use as an aortal prosthesis, wherein one of said leaflets having a larger cross-sectional area comprises a dorsal section of said valve and one of said leaflets having a smaller cross-sectional area comprises a ventral section of said valve.

6. A bi-leaflet prosthetic heart valve according to claim 1, wherein said flow channel includes a larger dorsal section and a smaller ventral section, wherein said valve is adapted for use as a mitral prosthesis, wherein one of said leaflets having a larger cross-sectional area comprises a dorsal section of said valve and one of said leaflets having a smaller cross-sectional area comprises a ventral section of said valve.

7. A bi-leaflet prosthetic heart valve according to claim 1, wherein said axle includes two end portions and said valve ring includes two shaft bearings for receiving said end portions.

8. A bi-leaflet prosthetic heart valve according to claim 7, wherein said shaft bearings each comprise a recess formed in said valve ring.

9. A bi-leaflet prosthetic heart valve according to claim 8, wherein said recesses forming said shaft bearings each extend along an inner surface of said valve ring from an upstream side to a downstream side.

10. A bi-leaflet prosthetic heart valve according to claim 1, wherein each of said leaflets includes a curved edge section and a substantially straight section in the vicinity of said axle, each of said leaflets includes at least one integrally formed sleeve portion adjacent said straight portion, said sleeve portion including a bore, said axle extending through said bores of each of said leaflets.

11. A bi-leaflet prosthetic heart valve according to claim 10, wherein said axle includes an outside diameter only slightly smaller than an inside diameter of each of said bores thereby forming a narrow gap, said gap being sufficiently large to permit said leaflets to pivot about said axle, and said gap being sufficiently small to hinder an entrance of blood into said gap.

12. A bi-leaflet prosthetic heart valve according to claim 1, wherein;

each of said leaflets includes a curved edge section having an apex;

each of said leaflets also includes a substantially straight section in the vicinity of said axle;

each of said leaflets includes at least one integrally formed curved sleeve portion adjacent said straight portion, said sleeve portion including a bore, said axle extending through said bores of each of said leaflets; and at least one surface of each of said leaflets has a convex configuration extending from said apex to said straight section, said continuously curving into a curvature of said sleeve portion.

13. A bi-leaflet prosthetic heart valve according to claim 1, wherein each of said leaflets includes a curved edge section having an apex, and an aperture angle is defined by two lines passing through a longitudinal central axis of said axle and said apexes of said leaflets.

14. A bi-leaflet prosthetic heart valve according to claim 13, wherein said aperture angle is between about 10° and about 40° when said leaflets are in said open position.

15. A bi-leaflet prosthetic heart valve according to claim 13, wherein said aperture angle is between about 12° and about 18° when said leaflets are in said open position.

16. A bi-leaflet prosthetic heart valve according to claim 1, further comprising:

first stop means projecting toward a center of said valve ring and preventing said leaflets from pivoting beyond a maximum open position; and second stop means projecting toward a center of said valve ring and preventing said leaflets from pivoting beyond a maximum closed position.

17. A bi-leaflet prosthetic heart valve according to claim 16, wherein said first stop means includes projecting step portions projecting toward said center of said valve ring and extending along an inner circumference of said valve ring on opposite sides of a location where said axle is secured to said valve ring in a direction substantially parallel to said valve ring.

18. A bi-leaflet prosthetic heart valve according to claim 17, wherein said step portions each have a length of from about 3 mm to about 6 mm.

19. A bi-leaflet prosthetic heart valve according to claim 16, wherein said second stop means comprises pins, projecting toward a center of said valve ring.

20. A bi-leaflet prosthetic heart valve according to claim 1, wherein at least one of said valve ring and said leaflets includes a multi-layered structure including an exterior layer including a pyrolytic carbon, at least one intermediate layer including a titanium carbide, and a core including metallic titanium.

21. A bi-leaflet prosthetic heart valve according to claim 1, wherein said leaflets are adapted to be moved between said closed position and said open position by blood flow within a heart that said bi-leaflet prosthetic heart valve is implanted into.

22. The bi-leaflet prosthetic heart valve according to claim 1, wherein the axle comprises two end portions wherein each end portion being retained in a shaft bearing formed like a recess in the valve ring;

wherein each shaft bearing comprises the form of a longitudinal recess extending from the left side below the valve ring plane to the right side above the valve ring plane.

23. The bi-leaflet prosthetic heart valve according to claim 22, wherein the valve ring comprises an inner circumference; and said inner circumference comprises at least in the area of the two shaft bearings a configuration or contour which widens in the direction of the blood flow.

24. The bi-leaflet prosthetic heart valve according to claim 22, wherein the valve ring comprises a greater height and/or a larger wide in the area of the shaft bearings than in the other sections of the valve ring.

25. The bi-leaflet prosthetic heart valve according to claim 1, wherein the axle comprises a two-part structure consisting of two axle portions;

wherein each axle portion comprises at one end a thickened head portion retained within a shaft bearing; and comprises at the other end an opposite end portion, wherein one opposite end portion being formed like a socket, and the other opposite end portion being formed like a pin, enabled to be inserted in said socket.

26. The hi-leaflet prosthetic heart valve according to claim 1, wherein the valve ring comprises at least one section of the greater height; and said section being arranged adjacent to the leaflet of smaller area.

* * * * *